US011191856B2

(12) United States Patent
Mancinelli et al.

(10) Patent No.: US 11,191,856 B2
(45) Date of Patent: Dec. 7, 2021

(54) VISIBLE-LIGHT ANTIMICROBIAL TREATMENT FOR HAND-HELD DEVICE

(71) Applicant: Datalogic IP Tech, S.r.l., Calderara di Reno (IT)

(72) Inventors: Paolo Mancinelli, Bologna (IT); Vito Lisma, Calderara di Reno (IT)

(73) Assignee: DATALOGIC IP TECH, S.R.L.

( * ) Notice: Subject to any disclaimer, the term of this patent is extended or adjusted under 35 U.S.C. 154(b) by 186 days.

(21) Appl. No.: 16/230,947

(22) Filed: Dec. 21, 2018

(65) Prior Publication Data
US 2020/0197549 A1    Jun. 25, 2020

(51) Int. Cl.
*A61L 2/08* (2006.01)
*H02J 7/00* (2006.01)
*A61L 2/24* (2006.01)

(52) U.S. Cl.
CPC .......... *A61L 2/084* (2013.01); *A61L 2/24* (2013.01); *H02J 7/0044* (2013.01); *H02J 7/0047* (2013.01); *A61L 2202/11* (2013.01); *A61L 2202/14* (2013.01)

(58) Field of Classification Search
CPC ........ A61L 2/084; A61L 2/24; A61L 2202/14; A61L 2202/11; H02J 7/0044; H02J 7/0047
See application file for complete search history.

(56) References Cited

U.S. PATENT DOCUMENTS 6,490,351 B1    12/2002    Roberts
9,700,641 B2    7/2017    Hawkins et al.
2003/0072676 A1*   4/2003    Fletcher-Haynes ......... A61L 2/0082 422/23
2004/0147293 A1*   7/2004    Park ......... H04M 1/17 455/573
2015/0071819 A1    3/2015    Todeschini
2016/0030612 A1    2/2016    Kim et al.
2016/0271659 A1    9/2016    Russ
2017/0190598 A1*   7/2017    Liao ......... C02F 1/725
(Continued)

FOREIGN PATENT DOCUMENTS

CN    202503309 U    10/2012
EP    3394841 A1    10/2018
(Continued)

OTHER PUBLICATIONS

A.J. De Lucca, (2012) Blue light (470 nm) effectively inhibits bacterial and fungal growth. Letters in Applied Microbiology, 55, 460-466.
(Continued)

*Primary Examiner* — Sean E Conley
*Assistant Examiner* — Brendan A Hensel
(74) *Attorney, Agent, or Firm* — Cozen O'Connor

(57) ABSTRACT

A station for a handheld information device (HID) includes a station body having a periphery and a receiving surface to support at least a portion of the HID. A visible antimicrobial illumination (VAI) emitter is coupled to the station body and arranged to direct a human-visible illumination beam at a target surface of the HID to produce an antimicrobial effect on the target surface. At least a first portion of the target surface is external to the periphery of the station body, and the human-visible illumination beam is projected beyond the periphery to illuminate the first portion of the target surface.

19 Claims, 7 Drawing Sheets

(56) References Cited

U.S. PATENT DOCUMENTS

| | | | |
|---|---|---|---|
| 2017/0296686 A1 | 10/2017 | Cole | |
| 2017/0348444 A1* | 12/2017 | Jang | ................. A61L 2/085 |
| 2018/0200396 A1* | 7/2018 | Messina | ................. A61L 2/24 |
| 2019/0005761 A1 | 1/2019 | Persici et al. | |
| 2019/0070324 A1 | 3/2019 | Hardin et al. | |

FOREIGN PATENT DOCUMENTS

| | | | |
|---|---|---|---|
| KR | 20170107801 A | 9/2017 | |
| WO | 2014181909 A1 | 11/2014 | |
| WO | WO-2017109800 A1 * | 6/2017 | ............. G07F 11/62 |

OTHER PUBLICATIONS

UV Brush Head Sanitizer HX7990/02, www.usa.philips.com/c-p/HX7990_02/sonicare-uv-brush-head-sanitizer, retrieved Dec. 11, 2018, 4 pages.

Tianhong Dai et al., Blue light for infectious diseases: Propionibacterium acnes, Helicobacter pylori, and beyond?, Author Manuscript Copy (Pub'd as Drug Resist Updat. Aug. 2012; 15(4): 223-236).

* cited by examiner

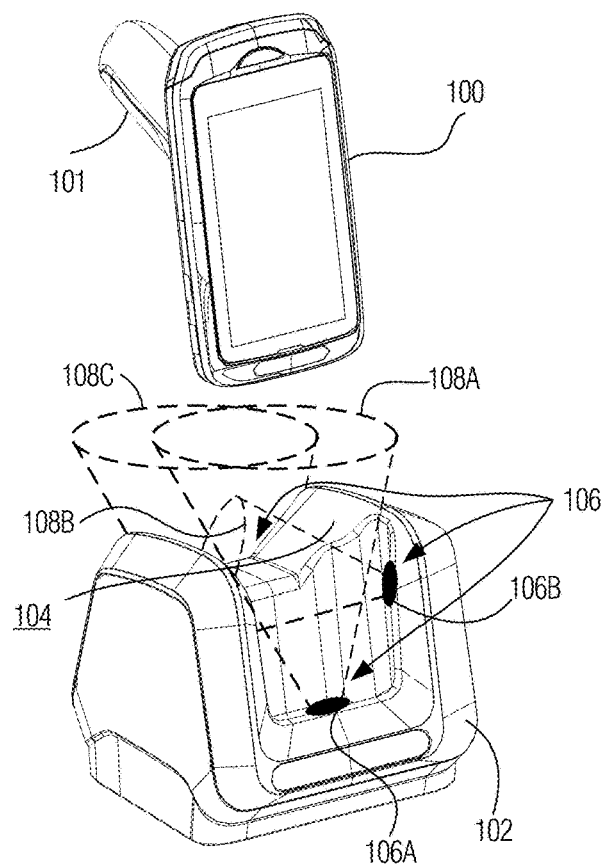
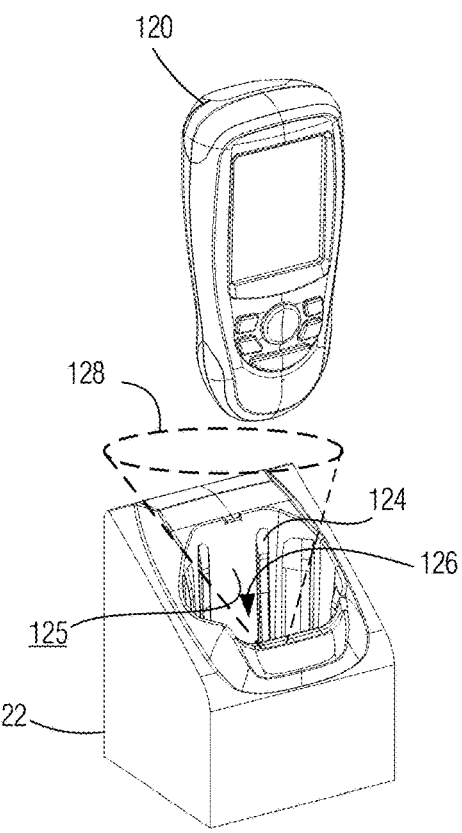
*FIG. 1A*
*FIG. 1B*
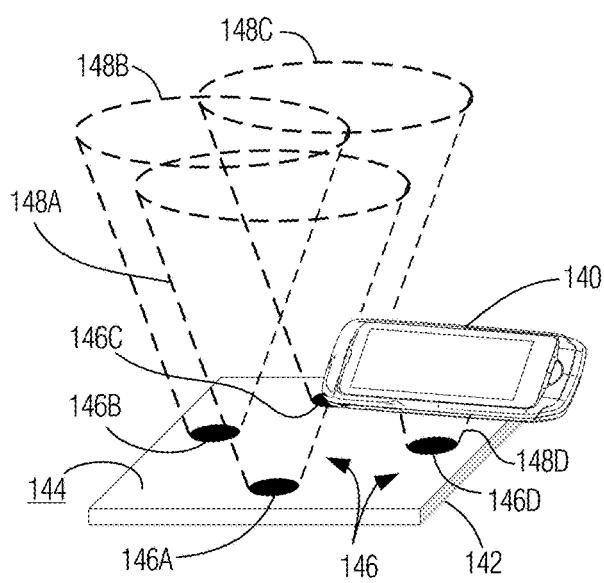
*FIG. 1C*

VISIBLE-LIGHT ANTIMICROBIAL TREATMENT FOR HAND-HELD DEVICE

TECHNICAL FIELD

Embodiments described herein generally relate to handling and storage of portable electronic devices and, more particularly, to charging or storage stations for portable devices that provide anti-microbial treatment to the devices.

BACKGROUND

Hand-held portable devices, such as smartphones, television remote controls, gaming controllers, computer mice, headsets, smart-glasses, and the like, are known vectors for spreading microbes. Increasingly, particularly in public settings such as retail, academic, office, warehousing, industrial, transportation, and healthcare environments, hand-portable devices of various types may be shared among multiple users. Generally, the palms of the hands are the human body parts with the highest concentrations of bacteria and other microbes; hence, objects handled by different people present considerable concerns for health and wellness of the public.

As just one example, devices with barcode-reading capability are commonly used as point-of-sale or self-shopping devices in retail establishments, and as data-entry devices for inventory/package tracking in warehouse and shipping applications. These types of devices may be handled by many different individuals during the course of the day, potentially exposing multiple users to pathogens left on the surfaces of the devices.

A variety of solutions to address this challenge have been proposed, including incorporating ultraviolet (UV) light sterilization in a charging cradle of a mobile device. The use of UV light presents several challenges. For one, UV light is generally harmful to humans and other animals, necessitating the use of protective enclosures or other safety provisions. In addition, UV light tends to degrade plastics, paint, and other materials from which mobile devices are made. Repeated sterilization cycles may accelerate the aging of these devices and adversely affect their long-term quality and durability.

Recently, light from the visible spectrum, particularly blue light, has been shown to provide an antimicrobial effect. The use of blue light has been proposed for use in disinfecting mobile devices, and would advantageously avoid some of the aforementioned drawbacks associated with UV-spectrum light. The use of blue light for its antimicrobial effect still presents number of challenges. For instance, the energy level and antimicrobial efficacy of blue light compared to UV light is reduced, meaning that visible blue light cannot simply be substituted in place of UV-based antimicrobial illumination treatments and remain equally effective.

Practical solutions are needed to facilitate the effective use of visible light in mobile-device treatment applications.

SUMMARY

Aspects of the embodiments are generally directed to a station for a handheld information device (HID), and to methods for operating such a station.

According to one aspect, a station includes a station body having a periphery and including a receiving surface to support at least a portion of the HID. A visible antimicrobial illumination (VAI) emitter is mechanically coupled to the station body and arranged to direct a human-visible illumination beam at a target surface of the HID when the HID is operatively engaged with the receiving surface. The human-visible illumination beam is to produce an antimicrobial effect on the target surface. At least a first portion of the target surface is external to the periphery of the station body, and the human-visible illumination beam is projected beyond the periphery to illuminate the first portion of the target surface.

According to another aspect, the station is a charging station that includes a charging circuit to supply power for charging a battery of the HID according to a charging program. A VAI emitter is mechanically coupled to the station body and arranged to direct a human-visible illumination beam at a target surface of the HID when the HID is operatively engaged with the receiving surface. The human-visible illumination beam is to produce an antimicrobial effect on the target surface according to an antimicrobial treatment program. At least a portion of the human-visible illumination beam is directed beyond the periphery to provide a visual indicator to a human operator, with the visual indicator relating to an operational aspect of the charging program or the HID.

A method for operating a station for a HID according to a related aspect includes supporting at least a portion of the HID on a structure of the station, and directing VAI as a human-visible illumination beam at a target surface of the HID from the structure of the station. The human-visible illumination beam is to produce an antimicrobial effect on the target surface. At least a first portion of the target surface is external to a periphery of the structure of the station; and the human-visible illumination beam is projected beyond the periphery to illuminate the first portion of the target surface.

A method for operating a charging station according to a related aspect includes supporting at least a portion of the HID by a structure of the charging station, supplying power for charging a battery of the HID according to a charging program, and controllably emitting visible antimicrobial illumination (VAI) from the station structure as a human-visible illumination beam directed at a target surface of the HID. The human-visible illumination beam is to produce an antimicrobial effect on the target surface according to an antimicrobial treatment program. At least a portion of the human-visible illumination beam is directed beyond a periphery of the charging station to provide a visual indicator to a human operator, with the visual indicator relating to an operational aspect of the charging program or the HID.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings.

FIG. 1A is a perspective-view diagram illustrating a charging station for a handheld information device (HID) that is a gun-style HID having a grip, according to some embodiments.

FIG. 1B is a diagram illustrating a partially-enclosed charging cradle-style HID station according to some embodiments.

FIG. 1C is a diagram illustrating a pad-style wireless charging station for HIDs according to some embodiments.

DETAILED DESCRIPTION

Figure 2:
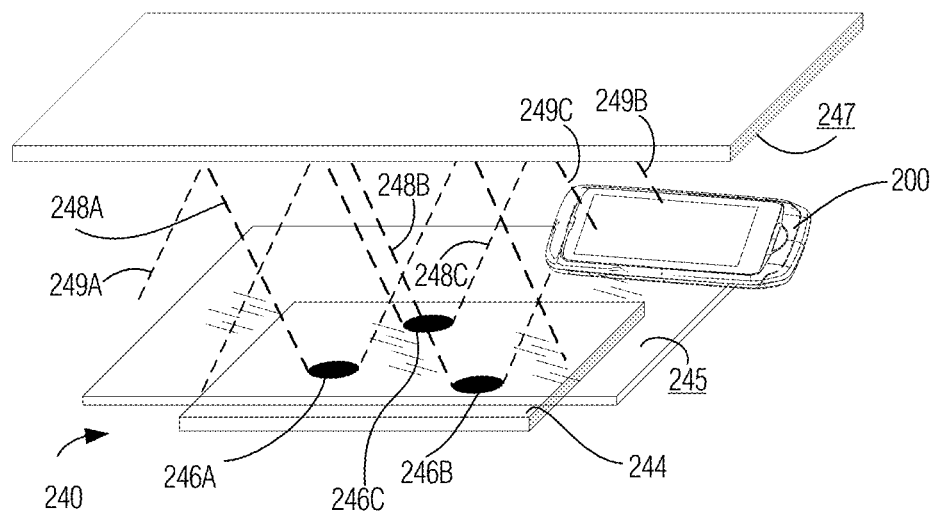
FIG. 2 is a simplified diagram illustrating various features and arrangements of a HID station facilitating visible antimicrobial illumination (VAI) administration, including transparent and reflective surfaces according to some embodiments.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Aspects of the embodiments are directed to a station for a handheld information device (HID) that includes an emitter of visible illumination to produce an antimicrobial effect. The visible antimicrobial illumination (VAI) is directed onto surfaces of the HID when the HID is operatively positioned on the station.

The HID station may be a charging station that couples power to the HID to charge its battery. In some embodiments of charging stations, the HID station may provide electrical contacts with which the HID may engage. In other charging-station embodiments, wireless charging may be facilitated. In other examples, the HID station may be simply a storage rack or cradle that serves as a home location and disinfection station for the HID, without including the charging provisions.

The HID station may have a HID-positioning structure that engages with a mating surface of the HID and maintains the HID in a stable resting position. The HID-positioning structure may include a recess, a protrusion, a guide, or other suitable structure. In another type of embodiment, the station omits any HID-positioning structure that enforces consistent positioning of the HID, and instead uses other provisions to facilitate suitable placement of the HID.

In some embodiments, the HID station provides a partial enclosure around the HID such that, when the HID is engaged with the station, a first portion of the HID is in the interior of the partial enclosure, and a second portion of the HID is outside of the partial enclosure. In related embodiments the VAI is concentrated in the interior of the partial enclosure, with a portion of the VAI radiating outward to the exterior of the partial enclosure with a sufficient intensity to provide an antimicrobial effect on surfaces of the second portion of the HID (extending past the periphery of the partial enclosure of the station).

According to a related type of embodiment, the HID station has a peripheral dimension, and when the HID is engaged with the station at least a portion of the HID protrudes beyond the peripheral dimension. In this type of embodiment, the VAI may be directed to illuminate portions of the HID within the periphery of the station, in addition to the one or more portions of the HID protruding beyond the periphery of the station.

In some embodiments, the HID station may include a plurality of VAI emitters positioned to provide suitable illumination of key targeted areas of the HID. In related embodiments, the HID station may include transparent materials in the vicinity of the VAI emitters or elsewhere to facilitate propagation of the VAI to various portions of the HID. In other related embodiments, reflective surfaces are included to re-direct or concentrate the VAI onto targeted surfaces of the HID for antimicrobial treatment. In further related embodiments, a light pipe or other type of waveguide is included in the HID station to redirect a portion of the VAI from its source emitter to a different region of the station facing a VAI-targeted surface of the HID. Still other embodiments may utilize lenses, reflective structures, or light-scattering structures to suitably illuminate targeted surfaces of the HID.

A related aspect of the embodiments is directed to a multi-HID station that is constructed to concurrently hold a plurality of HIDs. In some embodiments, a given VAI emitter may be arranged to illuminate a plurality of HIDs at the same time. Various transparent or reflective surfaces may be used in conjunction with suitable emitter placement to facilitate suitable illumination of targeted surfaces of the multiple HIDs.

In a related aspect of the embodiments, the HID station is autonomously controlled to provide an effective antimicrobial treatment program that lasts for a finite time duration. For instance, the duration of the VAI application may be dynamically variable based on measured or inferred prior usage of the HID since the previous VAI application. In a related embodiment, the VAI is coordinated with the charging program to provide effective disinfection while supporting usage availability of the HID.

In some embodiments, the VAI is used for a secondary purpose of providing visual information signaling or operational cues to a human operator in connection with the operation of the station or the HID. For example, the VAI may be used as an indicator that the HID is not ready for use. The VAI may be used as an indicator that the charging program is in process. The VAI may be used as an indicator that the HID has experienced a fault condition. The VAI may be used as an indicator that the HID is subject to a software/ firmware update. The VAI may be used as an indicator pertaining to establishment of communications between the HID and the station.

In a related embodiment, the VAI may be administered for a time duration that is longer than the time determined to be sufficient to complete the VAI program. Similarly, the VAI may be used to indicate a charging-in-process state even when the charging program is actually completed if the VAI program calls for continued VAI administration beyond the duration of the charging program.

Likewise, the VAI may be visibly pulsed, varied in perceived intensity, or otherwise modulated, according to a defined pattern to communicate relevant information to an operator. For example, different modulation patterns may be used to signal that the HID is properly positioned at the station or improperly positioned, that communications between the HID and the station are established or have failed, that the HID is undergoing VAI treatment or charging and is not ready for use, that the HID is charged to at least some defined amount, that the HID is charged and disinfected and ready for use, that there is a fault condition in connection with the charging or operational readiness of the HID, or the like.

In another related embodiment, different VAI emitters may be selectively activated or de-activated, or visibly pulsed in a defined pattern, to prompt the operator to re-position the HID on the station. As an example embodiment, a charging pad-style station may indicate that the HID can be re-positioned in a certain direction (e.g., to the left, right, forward or backward) for improved wireless-charging coupling or VAI effectiveness. In this example, VAI emitters situated around the HID may be selectively modulated to indicate the direction of re-positioning of the HID.

In yet another related embodiment, the VAI may be pulsed at an imperceptible rate according to known techniques to vary the perceived continuous brightness of the VAI while still providing effective antimicrobial performance. This embodiment may be employed to reduce the power consumption, or to vary the perceived intensity of the VAI without substantially reducing the effective antimicrobial performance. In the present context, substantial reduction of effectiveness corresponds to a statistically significant measured degradation of performance. The variable brightness of the VAI may be used as a mechanism of signaling the operator.

In various embodiments, the wavelength of the VAI may be in the range of 380 nm to 475 nm. For example, a nominal wavelength of 405 nm may be used. In related embodiments, additional colors of visible light may be emitted alongside the VAI to facilitate information signaling to the operator, or for aesthetic purposes. The added color can be used according to this type of embodiment without compromising the antimicrobial effect of the VAI wavelength.

FIGS. 1A-1C are perspective-view diagrams illustrating various styles of stations for HIDs. FIG. 1A illustrates a gun-style HID 100 that has grip 101. Station 102 in this example is a charging station having a form that is made to correspond with the exterior shape of HID 100. In particular, HID station 102 has a body that includes receiving surface 104 designed to mate with, and support grip 101 and portions of the underside of HID 100.

Station 100 includes a group of VAI emitters 106. As depicted, VAI emitter 106A is situated inside a recessed portion of station 100, and points upward to project illumination beam 108A as shown. VAI emitter 106B is positioned inside a lateral wall and in the recessed portion of station 100 to point sideways and produce illumination beam 108B. Another emitter of group 106 (not visible) is positioned towards the rear of station 100 and points upwards to produce illumination beam 108C as shown. Illumination beam 108C is directed towards grip 101 of HID 100.

Notably, when HID 100 is engaged with station 102, some portions of HID 100 are situated in the recessed portion of station 102 within its periphery, while other portions remain outside the periphery of station 102, the latter in particular extending above the upper periphery of station 102. VAI emitters 106 are arranged such that their collective illumination beams project outwards beyond the periphery of station 102 to illuminate at least some portions of HID 100 that are outside of the periphery of station 102.

FIG. 1B is a diagram illustrating a partially-enclosed charging cradle-style HID station 122 for HID 120. HID station 122 has a body that accommodates HID 120, which has a more compact form factor than HID 100. When HID 120 is engaged with charging cradle 122, a portion of HID 120 sits inside the partial enclosure. The interior of the partial enclosure includes alignment feature 124, which acts as a rail or spacer, and interior surface 125 that is shaped to accommodate HID 120. The interior of the partial enclosure also includes a VAI emitter 126 (not visible in FIG. 1B), which produces illumination beam 128 that extends out beyond the partial enclosure of station 122 to illuminate those portions of HID 120 that sit outside the partial enclosure. In various related embodiments, surface 125, may include a waveguide (e.g., light pipe) or a transparent wall to facilitate illumination of HID 120 with VAI.

Charging stations 102 and 122 may include electrical contacts that engage with mating contacts on respective HIDs 100 and 120 according to a wired-charging arrangement. In this type of charging connection, optional data communications between HIDs 100 and 120 and the respective charging stations 102 and 122 may be provided, and facilitated via the ohmic contacts. In another type of embodiment, wireless charging is facilitated according to electromagnetic coupling of the charging power between a power-transmitting transducer in station 102, 122, and a power-receiving transducer in HID 100, 120, respectively. In a wireless-charging arrangement, data communications between HIDs 100 and 120 and the respective charging stations 102 and 122 may be facilitated by wireless communications, such as radio-frequency (RF) communications, optical communications, sonic communications, or the like.

The examples of HID stations depicted in FIGS. 1A and 1B include one or more structural alignment features for ensuring correct or optimal placement of the respective HID. A structural alignment feature may include receiving surface 104 (FIG. 1A), alignment feature 124 (FIG. 1B), and interior surface 125 (FIG. 1B) that are formed to engage with an exterior surface or matching structural feature of the respective HID 100, 120.

FIG. 1C is a diagram illustrating a pad-style wireless charging station 142 for use with HID 140. Charging station 142 has a top receiving surface 144 on which HID 140 may be placed, and this receiving surface may include printed graphics or other visual indicia to assist the operator to properly place HID 140, but it otherwise lacks any structural alignment feature to enforce the proper placement. Charging station 142 includes a group of VAI emitters 146, including individual VAI emitters 146A-146D, which respectively produce illumination beams 148A-148D as shown.

According to some embodiments, VAI emitters 106, 126, and 146 as depicted in FIGS. 1A-1C are constructed from light-emitting diodes (LEDs) that emit one or more wavelengths in the visible spectrum that are known to have antimicrobial efficacy. For example, one or more wavelengths in the range of 380-475 nm may be used. In related embodiments, different LED devices producing different wavelengths within a range of wavelengths are combined in a single station to produce overlapping or non-overlapping illumination beams of different colors, with those colors optimized for efficacy against certain corresponding microbes.

In a related embodiment, VAI emitters 106, 126, and 146 further include a transparent housing portion, which may be formed as a lens, to produce a VAI illumination beam with a desired beam width. Different VAI emitters located at various distances from HID surfaces may use different beam widths to provide sufficient coverage of their respective targeted surface while concentrating the intensity of the VAI at the targeted location.

In another related embodiment, two or more LED devices having different wavelengths may be housed together in a single VAI emitter component package. The distinct LED devices may be individually or collectively controllable according to various examples.

FIGS. 2 and 3A-3C are simplified diagrams illustrating various features and arrangements facilitating VAI administration in a HID station according to several embodiments. FIG. 2 illustrates portions of HID station 240, which is a shown as a charging-pad type of station similar to station 142 (FIG. 1C), but may represent any sort of HID station such as charging-cradle types of HID stations depicted in FIGS. 1A and 1B. Station 240 includes base portion 244, which contains VAI emitters 246A-246C that produce, respectively, VAI illumination beams 248A-248C.

HID station 240 further includes transparent surface 245 situated between VAI emitters 246A-246C and HID 200. Transparent surface 245 may be formed from any suitable material, such as clear plastic (e.g., polycarbonate acrylate polymer, polyethylene terephthalate, etc.), glass, or the like. More generally, in related embodiments, transparent surface 245 may be formed as at least a portion of a surface that engages with the HID such as receiving surface 104 (FIG. 1A) or interior surface 125 (FIG. 1B). In some practical embodiments, transparent surface 245 may be used to separate HID 200 from VAI emitters 246A-246C so that illumination beams 248A-248C may cover larger areas on HID 200 as the beams spread out.

In related embodiments, HID station 240 includes reflective surface 247 arranged to redirect emitted VAI beams toward HID 200. Reflective surface 247 may form at least a portion of interior surface 125 (FIG. 1B) in partially-enclosed HID stations or, more generally, any HID-facing surface of an HID station. As depicted, reflective surface 247 functions to direct reflected beams 249A-249C toward the region where HID 200 is placed. The reflected beams may illuminate surfaces of HID 200 that are facing away from the VAI emitters or otherwise occluded from the incident VAI beams 248A-248C.

Figure 3A:
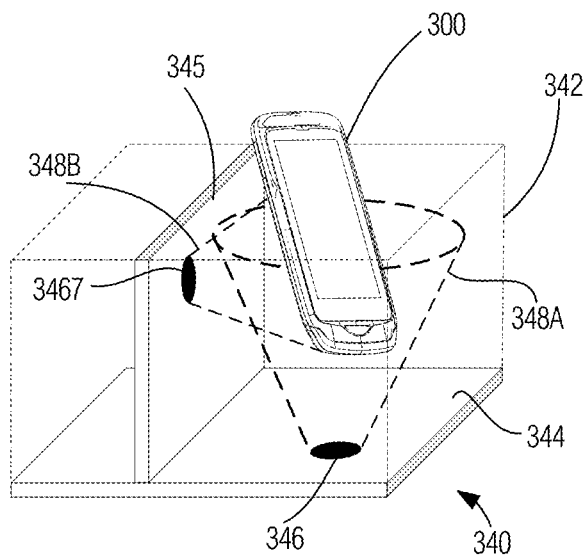
FIG. 3A is a simplified diagram illustrating various features and arrangements of a HID station facilitating VAI, including VAI emitters located on differently-oriented surfaces that project illumination beams beyond a periphery of the station according to some embodiments.

FIG. 3A is a simplified diagram illustrating example HID station 340 that has a periphery 342. In the present context, a periphery of a HID station is the outer-most axial or radial dimension of the station. In the configuration as illustrated, HID 300 is engaged with station 340, (receiving or mating surfaces are omitted from this diagram for clarity). HID 300 and station 340 are constructed and arranged such that a portion of HID 300 extends beyond periphery 342.

HID station 340 has a base portion 344 and a vertical portion 345. VAI emitter 346 is in base portion 344 and produces illumination beam 348A directed primarily upwards; VAI emitter 347 is in vertical portion 345 and produces illumination beam 348B directed primarily laterally. VAI illumination beams 348A and 348B may each propagate outwards beyond periphery 342 to treat surfaces of HID 300 that are beyond periphery 342, and to be seen by a human operator of HID station 340. In a related embodiment, a transparent surface such as surface 245 (FIG. 2), a reflective surface such as surface 247 (FIG. 2), or a combination of these features, may be incorporated in HID station 340 to enhance coverage of the VAI illumination for treated surfaces of HID 300, and also to provide a visual indication pertaining to the operation of station 340.

Figure 3B:
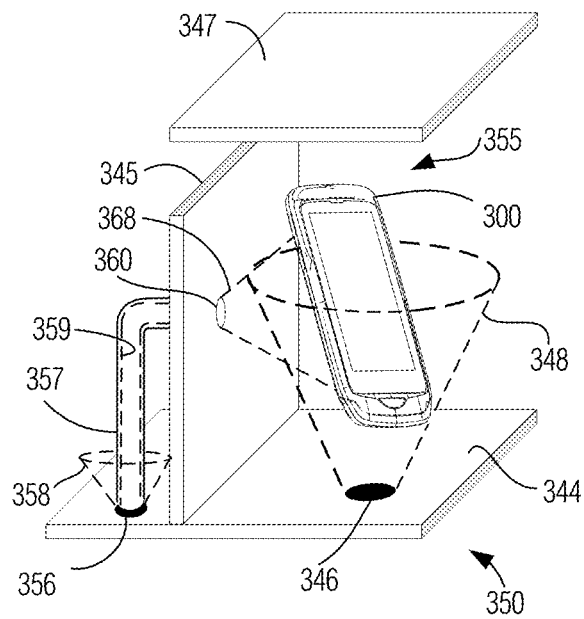
FIG. 3B is a simplified diagram illustrating various features and arrangements of a HID station facilitating VAI, including an optical waveguide according to some embodiments.

FIG. 3B is a simplified diagram illustrating HID station 350 according to a related embodiment, in which a VAI illumination beam is channeled using an optical guide. As illustrated, HID station 350 includes base portion 344, vertical portion 345, and top enclosure portion 347 defining interior space 355. A first VAI emitter 346 is inside interior space 355 and produces illumination beam 348 to target some surfaces of HID 300.

A second VAI emitter may be positioned inside or outside of interior surface 355. As illustrated, second VAI emitter 356 is situated outside of interior space 355 and produces illumination beam 358, which does not by itself reach a desired target surface of HID 300. Waveguide 357, which may be a light pipe, bundle of optical fibers, or other light-channeling structure, channels illumination flux 359 to be emitted as illumination beam 368 from waveguide outlet 360. Illumination beam 368 is therefore directed to a target surface of HID 300 that is otherwise obstructed due to the relative positioning of second VAI emitter 356 and HID 300, along with any occluding surfaces or objects interposed between second VAI emitter 356 and HID 300. A portion of illumination beam 358, emitted outside of interior space 355, is visible to an operator.

Notably, waveguides, such as waveguide 357 may be used with non-enclosed embodiments of HID stations. Likewise, waveguides may be used in conjunction with transparent surfaces or reflective surfaces, in any combination, to facilitate directing of the VAI at targeted surfaces of the HID on or in the station, or to project a portion of VAI out from the HID station to be observable by an operator.

Figure 3C:
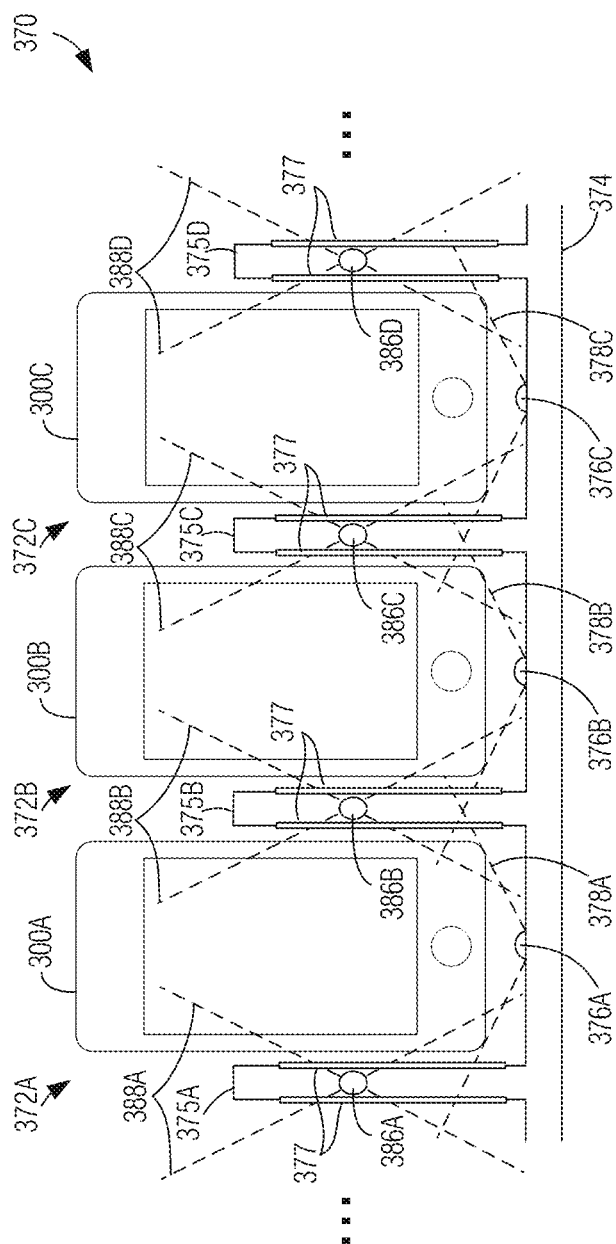
FIG. 3C is a simplified diagram illustrating a portion of a multi-HID station incorporating some aspects of the embodiments.

FIG. 3C is a simplified diagram illustrating a portion of a multi-HID station. As illustrated, multi-HID station 370 includes multiple docking sites 372A-372C (generally referenced as docking sites 372) for multiple HIDs 300A-300C. Although three docking sites are depicted, it will be understood that any practical number of docking sites may be provided according to various embodiments. Multi-hid station 370 includes base portion 374 and docking-site divider portions 375A-375D.

VAI emitters 376A-376C are provided in each docking site 372A-372C, and VAI emitters 386A-386D are provided between adjacent docking sites in docking-site divider portions 375A-375D. Transparent windows 377 may be provided as part of docking-site divider portions 375A-375D, as shown, or docking-site divider portions 375A-375D may be entirely formed from transparent material, according to various embodiments. Accordingly, each individual VAI emitter 386A-386D is configured to illuminate multiple docking sites 372. Each of VAI emitters 376A-376C may also illuminate more than one docking site 372.

As illustrated, VAI emitters 376A-376C produce illumination beams 378A-378C, respectively. Likewise, VAI emitters 386A-386D produce illumination beams 388A-388D, respectively. Illumination beams 378A-378C and 388A-388D each passes through corresponding windows 377 to illuminate one or more adjacent docking site 372. In addition, portions of the VAI emanate outwards from multi-HID station 374 to be observable by an operator.

In various related embodiments, a multi-HID station may incorporate various combinations of features described above, such as transparent surfaces, reflective surfaces, or waveguides to facilitate directing of the VAI at targeted surfaces of the HID on or in the station, or to project a portion of VAI out from the HID station to be observable by an operator.

Figure 4:
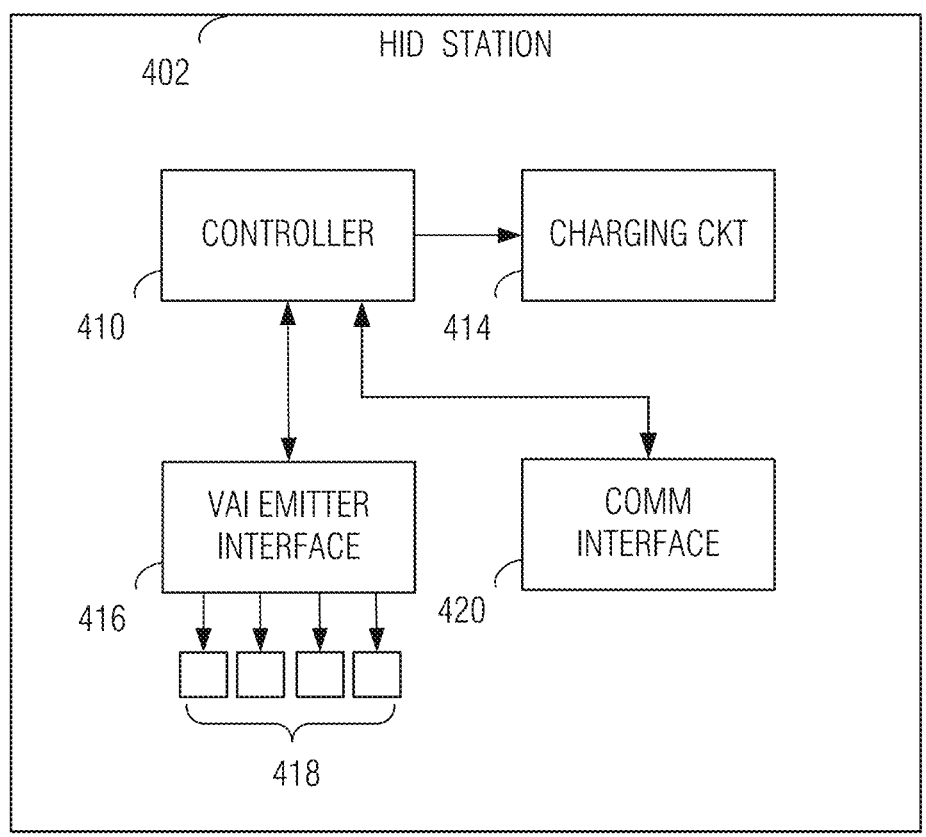
FIG. 4 is a block diagram illustrating an example functional architecture of a HID station according to some embodiments.

FIG. 4 is a block diagram illustrating an example functional architecture of a HID station according to some embodiments. As illustrated HID station 402 includes, among other electrical/electronic components, controller circuitry 410, charging circuitry 414, VAI emitter interface circuitry 416, VAI emitters 418, and communication interface circuitry 420.

Controller circuitry 410 includes a digital controller, such as a processor-based microcontroller, for example. Other implementations may be implemented with digital logic, such as with a programmable logic array (PLA), a field-programmable gate array (FPGA), or the like. Any suitable controller architecture is contemplated.

In a processor-based microcontroller embodiment, a microcontroller circuit may include a central processor unit (CPU) circuit, interrupt control circuitry, addressable memory circuitry, timer circuitry, and input/output circuitry. The CPU may include an arithmetic logic unit (ALU) circuit, an instruction decode and control unit (IDCU) circuit, a program counter circuit, instruction register, and general-purpose register circuitry. A variety of other processor-based microcontroller architectures may be used.

Charging circuitry 414 is controlled by controller circuitry 410. Charging circuitry 414 includes power-supply circuitry such as a linear regulator or switching regulator, to produce a suitable direct- or alternating-current supply of power that may be coupled to one or more HIDs for charging their battery.

VAI emitter interface circuitry 416 is coupled to a data bus or output port of controller circuitry 410, and is constructed to receive signaling from controller circuitry calling for activation or de-activation of individually-controllable VAI emitter devices. VAI emitter interface circuitry 416 includes circuitry to convert the received signaling into individually-switched power signals to the individually-controllable VAI emitters 418.

VAI emitters 418 are LEDs of suitable wavelength in the visible spectrum that provide an antimicrobial effect. As described above, in various embodiments, the wavelength of the VAI may be in the range of 380 nm to 475 nm. In related embodiments, additional colors of visible light (e.g., not necessarily having antimicrobial effect) may be emitted alongside the VAI to facilitate information signaling to the operator, or for aesthetics.

Communication interface circuitry 420 may include serial communications or RF and baseband circuitry for providing wired or wireless data communications between controller circuitry 410 and one or more HID devices engaged (or to be engaged) with HID station 402. Any suitable communications technology may be employed, such as one (or more) a wired serial data connection such as universal serial bus (USB), controller-area network (CAN), RS-232, or the like; or a wireless data communication technology, such as a RF-based technology selected from among the IEEE 802.11 family of standards, the IEEE 802.15 family of standards, ANT/ANT+, Z-Wave, Wireless USB, Zigbee, or the like. Other wireless technologies may be used, such as one based on optical signaling, or sonic/ultrasonic signaling, for example, or an optical data communications modality that uses light or laser technology to transmit data (for example IRDA or Li-Fi).

Communication interface circuitry 420 may be used to facilitate the transfer of information between the HID and the station pertaining to battery charging, disinfection operations, or application-level data relating to the principal operations of the HID.

Various operational embodiments are described in greater detail below that utilize the mechanical and electronic architectures of HID stations described up to this point. More particularly, examples of VAI control in concert with charging operations of a HID station are described. In addition, examples of communications pertaining to charging and disinfection operations using VAI are described below.

Figure 5:
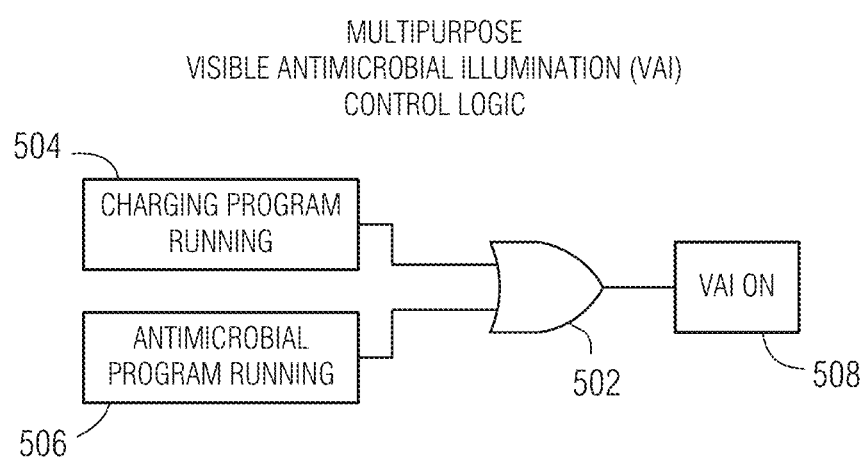
FIG. 5 is a simplified logic diagram illustrating an example of multipurpose usage of VAI according to an aspect of the embodiments.

FIG. 5 is a simplified logic diagram illustrating an example of multipurpose usage of VAI according to an aspect of the embodiments. According to this aspect, the VAI is used to (a) disinfect exterior surfaces of the HID, and (b) signal information to a human operator pertaining to the operation of the HID station or operational status of the HID.

In the example illustrated, a logical OR operation 502 is performed to consider the operational state of the charging program 504 and the operational state of the antimicrobial program 506 to activate or de-activate the VAI. More specifically, the VAI is activated at 508 when either or both of the charging program, or the antimicrobial program, is/are running. According to this logic, the VAI may be active even when the antimicrobial program is completed or not called for.

This example facilitates the use of the VAI as an indicator of "readiness" of the HID. Thus, the HID may be deemed ready for use when the VAI is off. Conversely, when the VAI is on, it is a signal to the operator that the HID is not ready for use. In related embodiments, various additional signaling schemes may be applied to indicate degree of readiness (e.g., battery is 25% charged/50% charged/75% charged/100% charged, and whether the antimicrobial program is either completed or not completed). With this information the operator may opt to use a limited-readiness HID and to take appropriate precautionary measures, such as applying an alternative form of disinfection (e.g., alcohol-based wipes), or taking measures to limit battery-energy consumption during ensuing use of the HID.

Figure 6:
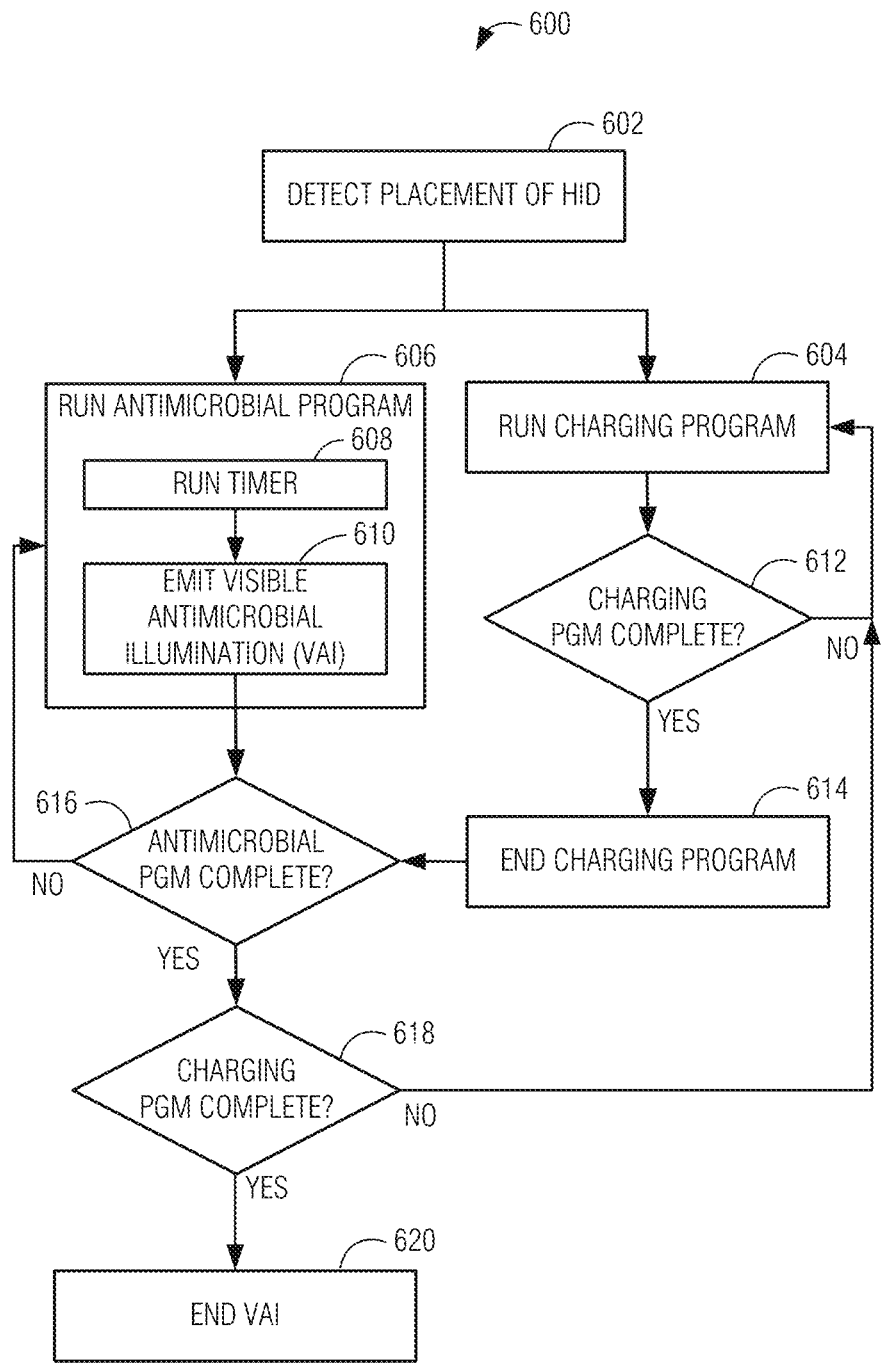
FIG. 6 is a process flow diagram illustrating VAI control according to an example embodiment.

FIG. 6 is a process flow diagram illustrating VAI control according to an example embodiment. Process 600 may be executed by controller circuitry 410 of HID station 402, for example. At 602, controller 410 detects the placement of the HID on or into the station. Detection of the HID placement may be achieved by measurement of the transfer of power to the HID by charging circuit 414. In addition, placement may be verified via communications between station 402 and the HID (e.g., if the HID reports receipt of transferred power approximately equal to the measured outgoing power as measured by charging circuit 414).

At 604, controller circuitry 410 runs the charging program. As an example, the charging program may involve determination of battery depletion, and control of a variable flow of current to the battery according to an optimized function to charge the battery at a preferred rate while preserving the longevity of the battery by minimizing undue wear from the charging process. The charging program may adjust the flow of current based on the battery type, the temperature of the battery, and on the prevailing conditions, such as the ambient temperature, and it may perform various measurements during the charging process to re-assess conditions and adjust the charging current.

At 606, controller circuitry 410 runs the antimicrobial program. As an example, the antimicrobial program may involve a determination of the time for VAI application at a given intensity level, or it may determine time and intensity of the VAI according to a determined VAI energy prescription. The amount of VAI to be applied (e.g., in terms of power and duration) may be based on prior usage of the HID since the last disinfection cycle. During the antimicrobial program, a timer is executed at 608, and the VAI is emitted at 610 at a fixed or variable intensity level.

At decision 616, a determination is made as to whether or not the antimicrobial program is completed. This determination may be based on the elapsed time since the start of the antimicrobial program, on the applied amount of VAI energy (measured or computed), or other determining factor or combination of factors. If the antimicrobial program is not complete, the process loops back to operation 606 to continue the antimicrobial program.

Turning to the charging program, at 612, a decision is made whether the charging program is complete. This decision may be based on passage of time since the start of the charging program, measured battery depletion level, measured charging current, or other factor or combination of factors. In the case that the charging program is incomplete, the process loops back to operation 604 to continue charging. Otherwise, if the charging is deemed complete, the charging program is ended at 614, and the process advances to decision 616 to check if the antimicrobial program is also completed.

Upon completion of the antimicrobial program, the process advances to decision 618 to verify whether the charging program is complete. This decision is redundant if the process arrived at this point having completed operation 614. However, if decision 616 was completed in the affirmative before completion of the charging program, decision 618 checks the completion of the charging program in the first instance. In the case where the charging program is not yet completed, the process loops back to 604 to continue charging while the VAI is continued (even though the antimicrobial program is deemed completed). Otherwise, upon verification that the charging program is completed at decision 618, the VAI is de-activated.

FIGS. 7A-7B, 8, and 9 are flow diagrams illustrating various operational sequences in determining an antimicrobial treatment parameter according to related embodiments. According to some examples, the antimicrobial treatment parameter may include duration of VAI application, energy of the VAI, or duration function of the VAI with respect to application intensity or duty cycle.

Figure 7A:
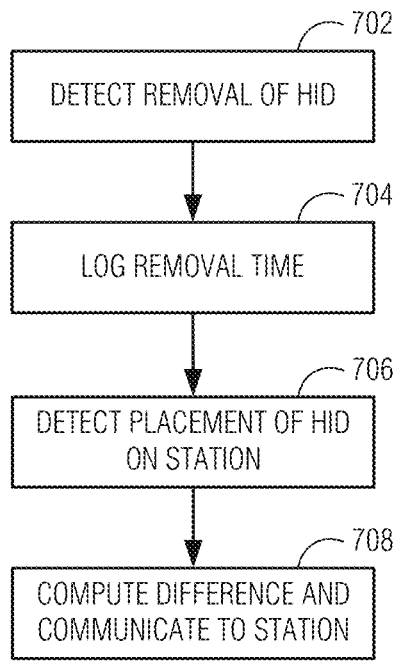
FIG. 7A is a process flow diagram illustrating operations performed by a HID to determine its time between antimicrobial treatments according to an example.

FIG. 7A is a process flow diagram illustrating operations performed by a HID to determine its time between antimicrobial treatments according to an example. At 702, the HID detects that it has been removed from its station. At 704 the time of removal is logged. At 706, the HID detects that it has been placed on a station. At 708, the HID computes the time difference to ascertain the duration of time that it has been away from the station, and communicates that information to the station.

Figure 7B:
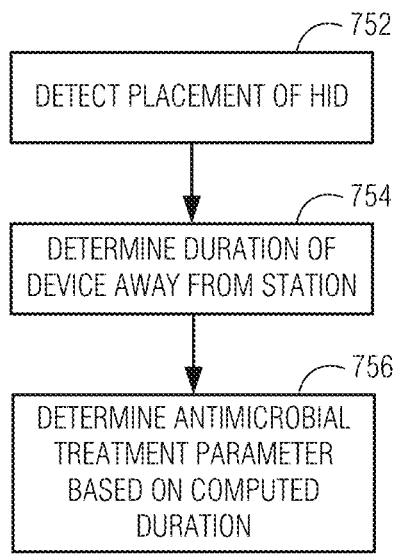
FIG. 7B is a process flow diagram illustrating operations performed by a HID station to determine an antimicrobial treatment parameter based on a duration of time that the HID was away from the station, according to an example.

FIG. 7B is a process flow diagram illustrating operations performed by a HID station, such as HID station 402, to determine an antimicrobial treatment parameter based on a duration of time that the HID was away from the station, according to an example. At 752, the station detects placement of the HID. At 754, the station determines the duration that the HID was away. This determination may be accomplished by receiving the relevant information from the HID, which had previously determined the duration based on the process of FIG. 7A. This approach supports applications where there may be multiple different stations by which the HID may be disinfected, and those stations do not share placement/removal log information.

In another example, the duration determination may be made by the station itself, based on logging the unique ID of the HID along with its placement and removal times, and computing the difference between the most recent placement and preceding removal. This example assumes that the HID was not placed on a different station that is not communicatively coupled with the first station's placement/removal log.

At 756, the station determines the antimicrobial treatment parameter based on the computed duration. As an example, the determination of the antimicrobial treatment parameter is based on a defined function represented as a formula or lookup table, for example, that relates VAI disinfection amount to estimated degrees of pathogen exposure. The removal-duration-based antimicrobial treatment parameter determination presupposes that during longer periods away from the station, the HID accumulates more pathogens.

Figure 8:
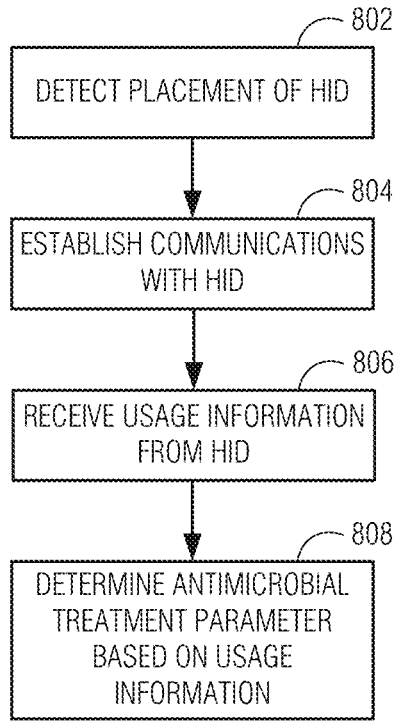
FIG. 8 is a process flow diagram illustrating operations performed by a HID station to determine an antimicrobial treatment parameter based on usage information, according to an example.

FIG. 8 is a process flow diagram illustrating operations performed by a HID station, such as HID station 402, to determine an antimicrobial treatment parameter based on usage information, according to an example. At 802, the station detects placement of the HID. At 804, the station establishes communications with the HID.

At 806, the station receives usage information from the HID. Usage information may include a count of the activations of the HID. For instance, where the HID is a barcode scanner, the count of activations may be incremented every time a barcode is scanned. Other measures of activations may include keypresses or touchscreen screen contacts. Other types of usage information may include a count of the number of times that the HID is picked up and set down. This data may be determined using an onboard accelerometer and logging instances of movement following periods of time when the HID has been stationary. For HIDs that require user login, the usage information may include a count of logins or a count of different users that logged in.

At 808, the station determines the antimicrobial treatment parameter based on the usage information. As with the duration-based example, the determination of the antimicrobial treatment parameter based on usage information may itself be based on a defined formula or lookup table that associates the relevant usage indicators with antimicrobial treatment parameter values.

Figure 9:
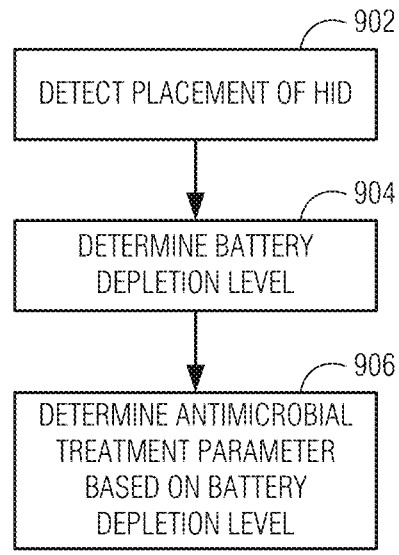
FIG. 9 is a process flow diagram illustrating operations performed by a HID station to determine an antimicrobial treatment parameter based on battery depletion level according to an example.

FIG. 9 is a process flow diagram illustrating operations performed by a HID station, such as HID station 402, to determine an antimicrobial treatment parameter based on battery depletion level according to an example. At 902, the station detects placement of the HID. at 904, the station determines the battery depletion level. This determination may be a part of the charging program—as when the charging program determines the state of the battery for purposes of deciding on the charging current and other variables.

At 906, the station determines the antimicrobial treatment parameter based on the battery depletion level. In this approach, the battery depletion level is an indicator of the amount of usage that the HID has undergone since its last charge. This approach presupposes that the antimicrobial treatment program and charging program are performed together every time the HID is placed on or in a station.

As with the duration-based and usage-based examples, the determination of the antimicrobial treatment parameter based on battery depletion level may be based on a defined formula or lookup table that associates the relevant battery level with antimicrobial treatment parameter values.

The examples illustrating variability of the antimicrobial treatment program work to support improved uptime of the HID. Accordingly, an HID that is determined to have experienced little usage (and hence fewer pathogen accumulation) since its last disinfection may be made more readily available (e.g., with a shorter duration of residence time at a station), compared to a HID that had experienced greater estimated pathogen accumulation, with the latter case calling for longer antimicrobial treatment.

In related embodiments that modulate the VAI for signaling or other purposes, the degree of antimicrobial treatment may or may not be varied as a consequence of different signaling patterns. In those cases where the signaling patterns affect the efficacy of the antimicrobial treatment, suitable corrections to the antimicrobial treatment program may be made automatically by the station.

Additional Notes and Examples:

Example 1 is a station for a handheld information device (HID), the station comprising: a station body having a periphery and including a receiving surface to support at least a portion of the HID; a visible antimicrobial illumination (VAI) emitter mechanically coupled to the station body and arranged to direct a human-visible illumination beam at a target surface of the HID when the HID is operatively engaged with the receiving surface; wherein the human-visible illumination beam is to produce an antimicrobial effect on the target surface; and wherein at least a first portion of the target surface is external to the periphery of the station body; and wherein the human-visible illumination beam is projected beyond the periphery to illuminate the first portion of the target surface.

In Example 2, the subject matter of Example 1 includes, wherein the station is a charging station that includes a charging circuit to supply power for charging a battery of the HID.

In Example 3, the subject matter of Examples 1-2 includes, wherein the body includes a transparent surface arranged to pass portions of the human-visible illumination beam to the first portion of the target surface.

In Example 4, the subject matter of Examples 1-3 includes, wherein the body includes a reflective surface arranged to direct portions of the human-visible illumination beam to the first portion of the target surface.

In Example 5, the subject matter of Examples 1-4 includes, wherein the body includes an optical waveguide structure arranged to direct portions of the human-visible illumination beam to the first portion of the target surface.

In Example 6, the subject matter of Examples 1-5 includes, wherein the body includes a partial enclosure that partially surrounds the HID when the HID is operatively engaged with the receiving surface.

In Example 7, the subject matter of Examples 1-6 includes, wherein the partial enclosure is formed such that, when the HID is operatively engaged with the station, a first portion of the HID is outside of the partial enclosure, and a second portion of the HID is in the interior of the partial enclosure, wherein the first portion of the target surface is a part of the first portion of the HID.

In Example 8, the subject matter of Examples 1-7 includes, wherein the station body is formed to include a plurality of docking sites for a corresponding plurality of HIDs, and wherein the VAI emitter is arranged to illuminate a plurality of HIDs when those HIDs are operatively engaged with their respective docking sites.

In Example 9, the subject matter of Example 8 includes, wherein the station body includes a plurality of docking site-specific VAIs, each docking site-specific VAI being situated to illuminate primarily a local HID when that local HID is operatively engaged with the respective docking site.

In Example 10, the subject matter of Examples 1-9 includes, a controller coupled to the VAI emitter and arranged to control operation of the VAI emitter according to a first antimicrobial treatment program, wherein the antimicrobial treatment program is to cause the human-visible illumination beam to produce the antimicrobial effect on the target surface for a finite first time duration.

In Example 11, the subject matter of Example 10 includes, wherein the controller is to autonomously vary an antimicrobial treatment parameter specific to the HID since completion of a previous antimicrobial treatment program administered to the same HID.

In Example 12, the subject matter of Example 11 includes, wherein the antimicrobial treatment parameter includes a treatment duration of the VAI.

In Example 13, the subject matter of Examples 11-12 includes, wherein the antimicrobial treatment parameter includes an illumination intensity of the VAI.

In Example 14, the subject matter of Examples 11-13 includes, wherein the controller is to dynamically vary the antimicrobial treatment parameter based on a time duration that is between completion of a preceding antimicrobial treatment program administered to the same HID, and initiation of the first antimicrobial treatment program.

In Example 15, the subject matter of Examples 11-14 includes, wherein the controller is to dynamically vary the antimicrobial treatment parameter based on HID-usage information communicatively received from the HID.

In Example 16, the subject matter of Examples 11-15 includes, wherein the controller is to dynamically vary the antimicrobial treatment parameter based on a measured battery depletion level of the HID.

In Example 17, the subject matter of Examples 11-16 includes, wherein the controller is to dynamically vary the antimicrobial treatment parameter based on an inference of pathogen accumulation on the target surface.

Example 18 is a charging station for a handheld information device (HID), the charging station comprising: a station body having a periphery and including a receiving surface to support at least a portion of the HID; a charging circuit to supply power for charging a battery of the HID according to a charging program; a visible antimicrobial illumination (VAI) emitter mechanically coupled to the station body and arranged to direct a human-visible illumination beam at a target surface of the HID when the HID is operatively engaged with the receiving surface; wherein the human-visible illumination beam is to produce an antimicrobial effect on the target surface according to an antimicrobial treatment program; wherein at least a portion of the human-visible illumination beam is directed beyond the periphery to provide a visual indicator to a human operator, the visual indicator relating to an operational aspect of the charging program or the HID.

In Example 19, the subject matter of Example 18 includes, wherein the visual indicator represents a HID-non-readiness state based on non-completion of the charging program and non-completion of the antimicrobial treatment program.

In Example 20, the subject matter of Examples 18-19 includes, wherein the antimicrobial treatment program is coordinated with the charging program such that the VAI is activated for a duration longer than a nominal time duration of the antimicrobial treatment program while the charging program runs.

In Example 21, the subject matter of Examples 18-20 includes, wherein the visual indicator is to provide a cue to the human operator relating to operation of the charging station or the HID.

In Example 22, the subject matter of Example 21 includes, wherein the cue relates to adjustment of positioning of the HID with respect to the charging station.

In Example 23, the subject matter of Example 22 includes, wherein the charging station includes a plurality of VAI emitters including said VAI emitter, and wherein the cue relating to the adjustment of positioning includes selective illumination of individual ones of the plurality of the VAI emitters corresponding to direction of positioning adjustment.

In Example 24, the subject matter of Examples 18-23 includes, wherein the visual indicator is to provide an indication of a fault condition relating to the HID.

In Example 25, the subject matter of Examples 18-24 includes, wherein the visual indicator is to provide an indication of a software/firmware update relating to the HID.

In Example 26, the subject matter of Examples 18-25 includes, wherein the visual indicator is to provide an indication of a software/firmware update relating to the HID.

In Example 27, the subject matter of Examples 18-26 includes, wherein the visual indicator is to provide an indication relating to data communications between the charging station and the HID.

In Example 28, the subject matter of Examples 18-27 includes, wherein the visual indicator is to be modulated according to a plurality of defined patterns to provide various different defined indications.

In Example 29, the subject matter of Example 28 includes, wherein the visual indicator is modulated in perceived intensity while substantially maintaining antimicrobial treatment effectiveness.

Example 30 is a method for operating a station for a handheld information device (HID), the method comprising: supporting at least a portion of the HID on a structure of the station; directing visible antimicrobial illumination (VAI) as a human-visible illumination beam at a target surface of the HID from the structure of the station; wherein the human-visible illumination beam is to produce an antimicrobial effect on the target surface; and wherein at least a first portion of the target surface is external to a periphery of the structure of the station; and wherein the human-visible illumination beam is projected beyond the periphery to illuminate the first portion of the target surface.

In Example 31, the subject matter of Example 30 includes, charging a battery of the HID by the station.

In Example 32, the subject matter of Examples 30-31 includes, autonomously controlling the VAI to provide a visual indicator to a human user, wherein the controlling includes: (a) pulsing the VAI; (b) varying intensity of the VAI; or (c) a combination of (a) and (b).

In Example 33, the subject matter of Examples 30-32 includes, autonomously controlling the VAI according to a first antimicrobial treatment program, wherein the antimicrobial treatment program is to cause the human-visible illumination beam to produce the antimicrobial effect on the target surface for a finite first time duration.

In Example 34, the subject matter of Example 33 includes, autonomously varying an antimicrobial treatment parameter specific to the HID since completion of a previous antimicrobial treatment program administered to the same HID.

In Example 35, the subject matter of Example 34 includes, wherein the antimicrobial treatment parameter includes a treatment duration of the VAI.

In Example 36, the subject matter of Examples 34-35 includes, wherein the antimicrobial treatment parameter includes an illumination intensity of the VAI.

In Example 37, the subject matter of Examples 34-36 includes, dynamically varying the antimicrobial treatment parameter based on a time duration that is between completion of a preceding antimicrobial treatment program administered to the same HID, and initiation of the first antimicrobial treatment program.

In Example 38, the subject matter of Examples 34-37 includes, dynamically varying the antimicrobial treatment parameter based on HID-usage information communicatively received from the HID.

In Example 39, the subject matter of Examples 34-38 includes, dynamically varying the antimicrobial treatment parameter based on a measured battery depletion level of the HID.

In Example 40, the subject matter of Examples 34-39 includes, dynamically varying the antimicrobial treatment parameter based on an inference of pathogen accumulation on the target surface.

Example 41 is a method for operating a charging station for a handheld information device (HID), the method comprising: supporting at least a portion of the HID by a structure of the charging station; supplying power for charging a battery of the HID according to a charging program; controllably emitting visible antimicrobial illumination (VAI) from the station structure as a human-visible illumination beam directed at a target surface of the HID; wherein the human-visible illumination beam is to produce an antimicrobial effect on the target surface according to an antimicrobial treatment program; wherein at least a portion of the human-visible illumination beam is directed beyond a periphery of the charging station to provide a visual indicator to a human operator, the visual indicator relating to an operational aspect of the charging program or the HID.

In Example 42, the subject matter of Example 41 includes, wherein the visual indicator represents a HID-non-readiness state based on non-completion of the charging program and non-completion of the antimicrobial treatment program.

In Example 43, the subject matter of Examples 41-42 includes, wherein the antimicrobial treatment program is coordinated with the charging program such that the VAI is activated for a duration longer than a nominal time duration of the antimicrobial treatment program while the charging program runs.

In Example 44, the subject matter of Examples 41-43 includes, wherein the visual indicator provides a cue to the human operator relating to operation of the method or the HID.

In Example 45, the subject matter of Example 44 includes, wherein the cue relates to adjustment of positioning of the HID with respect to the method.

In Example 46, the subject matter of Example 45 includes, wherein cue includes selective illumination of individual ones of the plurality of the VAI emitters corresponding to direction of positioning adjustment.

In Example 47, the subject matter of Examples 41-46 includes, wherein the visual indicator provides an indication of a fault condition relating to the HID.

In Example 48, the subject matter of Examples 41-47 includes, wherein the visual indicator provides an indication of a software/firmware update relating to the HID.

In Example 49, the subject matter of Examples 41-48 includes, wherein the visual indicator provides an indication of a software/firmware update relating to the HID.

In Example 50, the subject matter of Examples 41-49 includes, wherein the visual indicator provides an indication relating to data communications between the method and the HID.

In Example 51, the subject matter of Examples 41-50 includes, wherein the visual indicator is modulated according to a plurality of defined patterns to provide various different defined indications.

In Example 52, the subject matter of Example 51 includes, wherein the visual indicator is modulated in perceived intensity while substantially maintaining antimicrobial treatment effectiveness.

Example 53 is at least one machine-readable medium including instructions that, when executed by processing circuitry, cause the processing circuitry to perform operations to implement of any of Examples 1-52.

Example 54 is an apparatus comprising means to implement of any of Examples 1-52.

Example 55 is a system to implement of any of Examples 1-52.

Example 56 is a method to implement of any of Examples 1-52.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A station for a handheld information device (HID), the station comprising:
    a station body having a periphery and including a receiving surface to support at least a portion of the HID;
    a visible antimicrobial illumination (VAI) emitter mechanically coupled to the station body and arranged to direct a human-visible illumination beam at a target surface of the HID when the HID is operatively engaged with the receiving surface;
    wherein the human-visible illumination beam is to produce an antimicrobial effect on the target surface;
    wherein at least a first portion of the target surface is external to the periphery of the station body; and
    wherein the human-visible illumination beam is projected beyond the periphery to illuminate the first portion of the target surface and provide a visual indicator to a human operator, the visual indicator indicative of a HID-non-readiness state based on both non-completion of a charging program and non-completion of an antimicrobial treatment program; and
    wherein the human-visible illumination beam is further configured to be modulated according to a plurality of defined patterns for the visual indicator to provide various different defined indications to the human operator other than the non-completion of the charging program and the non-completion of the anti-microbial treatment program.

2. The station of claim 1, wherein the body includes an optical waveguide structure arranged to direct portions of the human-visible illumination beam to the first portion of the target surface.

3. The station of claim 1, wherein the body includes a partial enclosure that partially surrounds the HID when the HID is operatively engaged with the receiving surface.

4. The station of claim 1, wherein the partial enclosure is formed such that, when the HID is operatively engaged with the station, a first portion of the HID is outside of the partial enclosure, and a second portion of the HID is in the interior of the partial enclosure, wherein the first portion of the target surface is a part of the first portion of the HID.

5. The station of claim 1, wherein the station body is formed to include a plurality of docking sites for a corresponding plurality of HIDs, and wherein the VAI emitter is arranged to illuminate a plurality of HIDs when those HIDs are operatively engaged with their respective docking sites.

6. The station of claim 1, further comprising:
a controller coupled to the VAI emitter and arranged to control operation of the VAI emitter according to the antimicrobial treatment program, wherein the antimicrobial treatment program is to cause the human-visible illumination beam to produce the antimicrobial effect on the target surface for a finite first time duration.

7. A charging station for a handheld information device (HID), the charging station comprising:
a station body having a periphery and including a receiving surface to support at least a portion of the HID;
a charging circuit to supply power for charging a battery of the HID according to a charging program;
a visible antimicrobial illumination (VAI) emitter mechanically coupled to the station body and arranged to direct a human-visible illumination beam at a target surface of the HID when the HID is operatively engaged with the receiving surface;
wherein the human-visible illumination beam is to produce an antimicrobial effect on the target surface according to an antimicrobial treatment program;
wherein at least a portion of the human-visible illumination beam is directed beyond the periphery to provide a visual indicator to a human operator, the visual indicator indicative of a HID-non-readiness state based on both non-completion of the charging program and non-completion of the antimicrobial treatment program; and
wherein the human-visible illumination beam is further configured to be modulated according to a plurality of defined patterns for the visual indicator to provide various different defined indications to the human operator.

8. The charging station of claim 7, wherein the antimicrobial treatment program is coordinated with the charging program such that the VAI is activated for a duration longer than a nominal time duration of the antimicrobial treatment program while the charging program runs.

9. The charging station of claim 7, wherein the human-visible illumination beam is modulated in perceived intensity while substantially maintaining antimicrobial treatment effectiveness.

10. The station of claim 1, wherein the VAI has a wavelength in a range of 380 nm to 475 nm.

11. The station of claim 6, wherein the finite first time duration is determined based, at least in part, on at least one a unique ID of the HID.

12. The station of claim 11, wherein the finite first time duration is further based on placement/removal log information associated with the unique ID of the HID.

13. The station of claim 6, wherein the controller is configured to autonomously control the VAI including:
(a) pulsing the VAI;
(b) varying intensity of the VAI; or
(c) a combination of (a) and (b).

14. The station of claim 6, wherein the controller is further configured to autonomously vary an antimicrobial treatment parameter specific to the HID since completion of a previous antimicrobial treatment program administered to the same HID.

15. The station of claim 14, wherein the antimicrobial treatment parameter includes:
(a) a treatment duration of the VAI;
(b) an illumination intensity of the VAI; or
(c) a combination of (a) and (b).

16. The station of claim 14, wherein the controller is further configured to dynamically vary the antimicrobial treatment parameter based on a time duration that is between completion of a preceding antimicrobial treatment program administered to the same HID, and initiation of the first antimicrobial treatment program.

17. The station of claim 14, wherein the controller is further configured to dynamically vary the antimicrobial treatment parameter based on:
(a) HID-usage information communicatively received from the HID;
(b) a measured battery depletion level of the HID; or
(c) a combination of (a) and (b).

18. The charging station of claim 7, wherein the plurality of defined patterns include at least one of:
a first pattern indicative of the HID being properly positioned within the charging station;
a second pattern indicative of communications between the HID and the charging station are established or failed; or
a fourth pattern indicative of the HID being at least partially charged to a defined amount.

19. A charging station for a handheld information device (HID), the charging station comprising:
a station body having a periphery and including a receiving surface to support at least a portion of the HID;
a charging circuit to supply power for charging a battery of the HID according to a charging program;
a visible antimicrobial illumination (VAI) emitter mechanically coupled to the station body and arranged to direct a human-visible illumination beam at a target surface of the HID when the HID is operatively engaged with the receiving surface;
wherein the human-visible illumination beam is to produce an antimicrobial effect on the target surface according to an antimicrobial treatment program;
wherein at least a portion of the human-visible illumination beam is directed beyond the periphery to provide a visual indicator to a human operator, the visual indicator indicative of a HID-non-readiness state based on both non-completion of the charging program and non-completion of the antimicrobial treatment program; and
wherein the human-visible illumination beam is further configured to provide a visual indicator indicative of HID-non-readiness state based on a software/firmware update of the HID.

* * * * *